United States Patent [19]

Zabotto et al.

[11] Patent Number: 4,732,692

[45] Date of Patent: Mar. 22, 1988

[54] COSMETIC CLEANSING COMPOSITION

[75] Inventors: Arlette Zabotto, Paris; Jean-Claude Contamin, Morangis, both of France

[73] Assignee: L'Oreal, Paris, France

[21] Appl. No.: 854,817

[22] Filed: Apr. 23, 1986

[30] Foreign Application Priority Data

Apr. 23, 1985 [FR] France .................. 85 06125

[51] Int. Cl.$^4$ .................. C11D 3/48
[52] U.S. Cl. .................. 252/106; 252/542; 252/545; 252/546; 252/174.24; 252/174.21; 252/DIG. 5
[58] Field of Search .............. 252/547, 546, 545, 542, 252/106, 174.17, 174.24, 174.21, DIG. 5; 514/846

[56] References Cited

U.S. PATENT DOCUMENTS 4,543,205  9/1985  Contamin ..................... 252/546

FOREIGN PATENT DOCUMENTS 366689  9/1984  United Kingdom .

OTHER PUBLICATIONS

Chemical Abstracts, vol. 96, No. 18, May 1982, p. 404, ref. no. 148957v.
Klein et al.: "Synergistic Interactions of Anionic/Amphoteric Surfactants in Cosmetics" & Drug Cosmet. Ind., 1981, 129(6), 38, 40, 42, 76-2.

Primary Examiner—Josephine Barr
Attorney, Agent, or Firm—Cushman, Darby & Cushman

[57] ABSTRACT

This cosmetic composition contains from 0.05 to 3% by weight of at least one amphoteric surface-active agent chosen from the compounds of formulae (I), (IV), (V), (VI) and (VII), from 0.05 to 3% by weight of at least one anionic surface-active agent chosen from the compounds of formula (VIII) to (XI) and from 0.02 to 8% by weight of at least one nonionic polymer (poly-$\beta$-alanine, alkyl and hydroxyalkylcelluloses, starch derivatives) and/or anionic polymers (polyacrylamide, polyacrylamidosulphonic acid and its salts, sodium polymethacrylate), the total concentration of surface-active agent(s) not exceeding 5% by weight. Despite this reduced concentration of surface-active agent(s), which endows it with a satisfactory innocuousness, this composition has an excellent cleansing power.

16 Claims, No Drawings

COSMETIC CLEANSING COMPOSITION

The present invention relates to a new cosmetic cleansing composition, in particular a lotion for removing eye make-up in which the concentration of cleansing agent is substantially reduced compared to the known lotions for removing eye make-up, although without its cleansing power being diminished thereby.

As a general rule, cleansing agents which are used in the preparation of compositions for removing eye make-up consist of a mixture of surface-active agents. However, attempts are being made to limit the concentration of surface-active agents in the make-up remover lotion because, if they are present in excessive quantity, there is a danger that they may cause eye discomfort, that is to say an irritation or a smarting sensation in the eyes. However, this reduction in the quantity of surface-active agents must not be associated with a reduction in the make-up-removal properties.

The applicant has found, in a wholly surprising manner, that when a given proportion of at least one nonionic polymer and/or of an anionic polymer belonging to perfectly defined groups is used in cleansing compositions, especially for the removal of eye make-up, in which the cleansing agent consists of a particularly effective mixture of specific anionic and amphoteric surface-active agents, the concentrations of the two suface-active agents could be substantially reduced without however, affecting the properties of the composition, especially in respect of its cleansing power.

It has been found, furthermore, that the resulting compositions have the additional advantages of being very convenient cosmetically, that is to say that they do not tend to stick the eyelashes and the eyelids of the users, and of not giving rise to the problems caused by the instability of some of their ingredients, especially of the surface-active agents used, so as to provide an outstanding stability not only in storage, but also over wide ranges of temperatures.

The present invention consequently relates to the novel industrial product consisting of a cosmetic cleansing composition, especially for the removal of eye make-up, characterized in that it contains, in an aqueous solution:

(1) from 0.05 to 3% by weight, as active substance of at least one amphoteric surface-active agent taken from the group consisting of:
the compounds of formula (I):

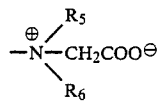

in which:
n is between 1 and 3;
$R_1$ denotes a fatty chain containing from 7 to 17 carbon atoms; and
$R_2$ denotes a residue of formula (II) or (III):

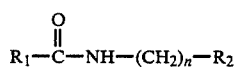   (II)

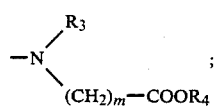   (III)

in which:
m is 1 or 2;
$R_5$ denotes a residue $-CH_2CH_2OR_4$ or a residue $-CH_2CH_2OCH_2CH_2COOR_4$;
$R_4$ denotes a hydrogen atom or an alkali metal;
$R_5$ denotes a $C_1-C_2$ alkyl or hydroxyalkyl residue; and
$R_6$ denotes a $C_1-C_2$ alkyl or hydroxyalkyl residue or a residue $-(CH_2)_mCOOR_4$, m and $R_4$ having the meaning given above;
the compounds of formula (IV):

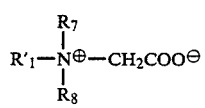

in which:
$R'_1$ denotes a fatty chain containing from 8 to 18 carbon atoms;
$R_7$ and $R_8$ denote, independently, a $C_1-C_2$ alkyl residue; and
the compounds of formula (V), (VI) or (VII):

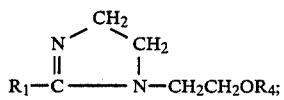   (V)

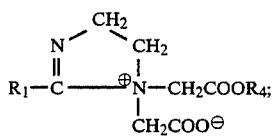   (VI)

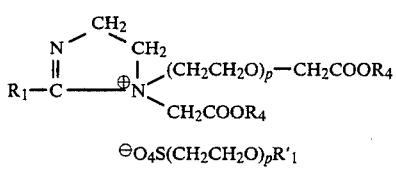   (VII)

in which
$R_1$, $R'_1$ and $R_4$ have the meanings given above; and
p is from 0 to 4;

(2) from 0.05 to 3% by weight as active material of at least one anionic surface-active agent taken from the group consisting of the compounds of formula (VIII), (IX), (X) or (XI):

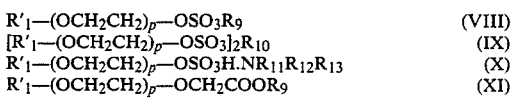

in which:
$R'_1$ and p have the meanings given above;
$R_9$ denotes an alkali metal;
$R_{10}$ denotes an alkaline-earth metal;
$R_{11}$, $R_{12}$ and $R_{13}$ independently denote a hydrogen, a $C_1-C_3$ alkyl residue or a $C_1-C_3$ hydroxyalkyl residue;

(3) from 0.02 to 8% by weight of at least one nonionic polymer taken from the group consisting of poly-$\beta$-alanines, ($C_1$–$C_3$-alkyl)celluloses, polyhydroxy($C_1$–$C_3$-alkyl)celluloses, polyvinylpyrrolidone, nonionic starch derivatives and hydroxypropylated derivatives of guar gum, and/or at least one anionic polymer taken from the group consisting of polyacrylamides containing carboxylate groups, polyacrylamidosulphonic acid and its salts, and the polymers and homopolymers of acrylic or methacrylic acid and their salts, with a molecular weight of less than 100,000, on condition that the total concentration of the surface-active agents in the composition does not exceed 5% by weight, the above percentages being calculated relative to the total weight of the composition.

In accordance with a preferred embodiment of the present invention, the composition contains:
from 0.1 to 2% by weight of the amphoteric surface-active agent(s);
from 0.1 to 2% by weight of the anionic surface-active agent(s);
from 0.05 to 5% by weight of the nonionic polymer(s) and/or of the anionic polymer(s).

Preferably, in the above formulae (I), (V) and (VI), $R_1$ denotes a $C_{11}$–$C_{13}$ fatty chain, and in the above formulae (IV) and (VIII) to (XI), $R'_1$ denotes a $C_{12}$–$C_{14}$ fatty chain.

Among the amphoteric surface-active agents which may be employed, there may be mentioned:
the compound denoted by the formula:

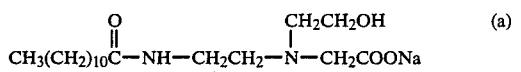
(a)

this compound being present in the commercial product sold by the company "Miranol" under the trade name "Miranol MHT",
the following compounds, in which the radical R denotes a residue of coprah fatty acids:

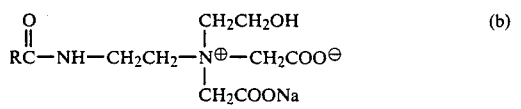
(b)

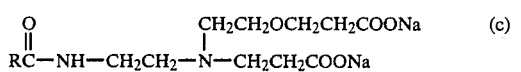
(c)

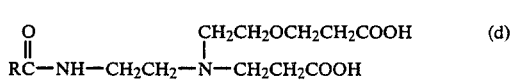
(d)

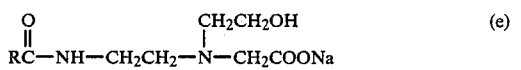
(e)

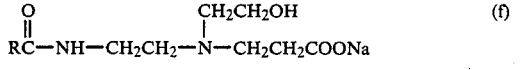
(f)

sold by the company "Miranol" under the trade names, respectively, of:
"Miranol C2M Conc. N.P." (or "Miranol C2M Conc. O.P."; or else "Miranol CM Special");
"Miranol C2M-SF 70%, C2M-SF 75%, C2M-SF Conc., C2M-SFE Conc. or C2M-SFP";
"Miranol C2M Anhydrous acid";
"Miranol CM Conc. N.P."; and
"Miranol CM-SF Conc." (or "Miranol CM-SFX Conc.");
the following compound in which R denotes a residue of coprah fatty acids:

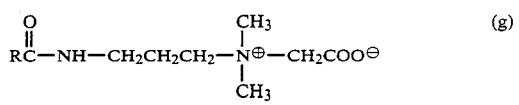
(g)

sold by the company "Henkel" under the trade name "Dehyton K",
the compound of formula:

(h)

sold by the company "Henkel" under the trade name "Dehyton AB-30",
the following compound in which R denotes a residue of coprah fatty acids:

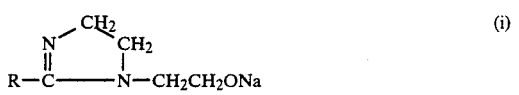
(i)

sold by the company "Henkel" under the trade name "Dehyton G";
the following compound in which R denotes a residue of coprah fatty acids:

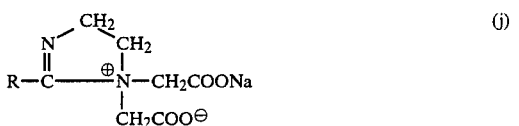
(j)

sold by the company "Naarden" under the trade name "Ampholak XCO-30";
the compound denoted by the formula:

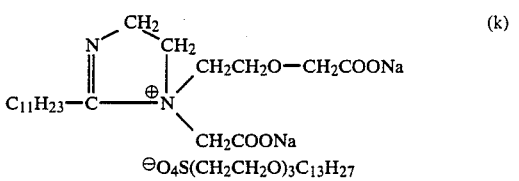
(k)

this compound being present in the commercial products sold by the company "Miranol" under the trade name "Miranol 2MHT modified".

Among the anionic surface-active agents, it is possible to mention in particular those which are denoted by the following formulae, in which n is from 1 to 4:

(l)

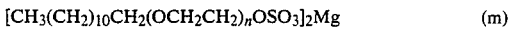
(m)

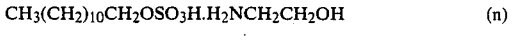
(n)

$$CH_3(CH_2)_{10}CH_2(OCH_2CH_2)_nOSO_3H \cdot H_2NCH_2-\underset{\underset{OH}{|}}{CHCH_3} \quad (o)$$

$$CH_3(CH_2)_{10}CH_2OSO_3Na \quad (p)$$

$$CH_3(CH_2)_{12}CH_2(OCH_2CH_2)_nOSO_3Na \quad (q)$$

$$CH_3(CH_2)_{10}CH_2(OCH_2CH_2)_nOSO_3H \cdot N(CH_2CH_2OH)_3 \quad (r)$$

$$CH_3(CH_2)_{10}CH_2(OCH_2CH_2)_nOCH_2COONa \quad (s)$$

which are marketed by the company "Henkel" under the trade names, respectively, of:
"Texapon A-400";
"Texapon MG";
"Texapon MLS";
"Texapon IES" (or "Texapon WW99");
"Texapon K12" (or K-1296, L-100, V HC Needles, ZHC Needles, ZHC Powder");
"Texapon K14S Special";
"Texapon NT"; and
by the company "Sandoz" under the trade name "Sandopan LS-24".

It is also possible to mention, as an anionic surface-active agent, the company of formula:

$$C_{13}H_{27}(OCH_2CH_2)_nOSO_3Na \quad (t)$$

in which n=1 to 4, this compound being present in the commercial products sold by the company "Miranol" under the trade names "Miranol 2MCT Modified, 2MHT Modified, BT Modified or MHT".

Among the nonionic polymers which may be used in the compositions according to the invention, there may be mentioned, in particular:

(1) Poly-beta-alanines described in Belgian Pat. No. 893,738.

These compounds contain from 50 to 100% of repeat units of the β-alanine type, corresponding to the following formula:

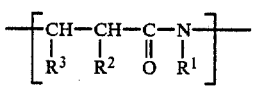

and from 0 to 50% of repeat units of the acrylamide type corresponding to the following formula:

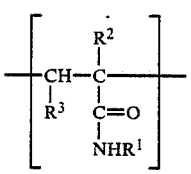

in which formulae:
$R^1$ denotes a hydrogen atom or a radical taken from the group consisting of the following radicals:

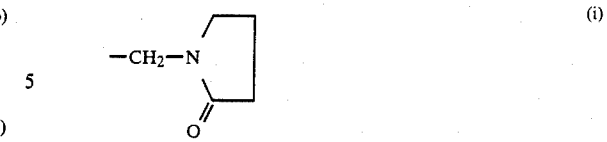

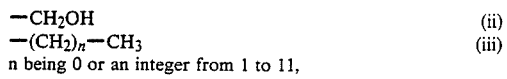
n being 0 or an integer from 1 to 11,

r' and r", which are identical or different, independently denoting a hydrogen atom or a $C_1$-$C_3$ alkyl radical,

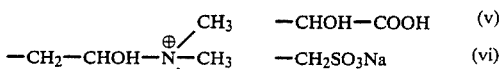

m being from 1 to 10; and $R^2$ and $R^3$ denote a hydrogen atom or a methyl radical.

These polymers are prepared by the polymerization of acrylamide, as described in U.S. Pat. No. 4,082,730. Preferably, they have a molecular weight of between 500 and 200,000 and, more especially between 2,000 and 100,000.

(2) Polyvinylpyrrolidone of a molecular weight of approximately 40,000, such as that sold by the company "GAF" under the trade name "PVP K-30";

(3) Hydroxyethylcellulose such as, for example, the substance sold under the trade name "Natrosol 250" by the company "Hercules";

(4) Hydroxypropyl derivatives of guar gum, especially the product sold by the company "Meyhall" under the trade name "Jaguar HP-8".

Among the anionic polymers which may be used in the compositions according to the invention, there may be mentioned, in particular:

1. Polyacrylamides containing carboxylate groups, such as those sold by the company "American Cyanamid" under the trade name "Cyanamer A 370";

2. Salts of polyacrylamidesulphonic acid, such as those mentioned in U.S. Pat. No. 4,128,631, and especially those of polyacrylamidomethylpropanesulphonic acid, such as that sold by the company "Henkel" under the trade name "Cosmedia Polymer HSP 1180" and consisting of a linear alkyl chain with pendent moieties which are amidomethylpropanesulphonic acid groups, as shown below:

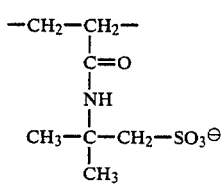

3. Sodium polymethacrylate, such as that sold by the company "Vanderbilt" under the trade name "Darvan No. 7", and 4. acrylic acid polymers such as that sold by the company "Allied Colloids" under the trade name "Versicol E5" and having a molecular weight of approximately 3500.

The carrier in the cleansing compositions according to the invention is either sterile demineralized water or a "floral" water such as rose water, cornflower water, camomile water, or lime water.

The other ingredients of the cleansing composition according to the invention are essentially: a preserving agent, which may be, for example, sodium ethylmercurythiosalicylate, a chlorohexidine salt such as the digluconate, diacetate and dihydrochloride, a phenylmercury salt such as phenylmercury nitrate, a mixture consisting of 30% by weight of sodium benzoate and 70% by weight of monochloroacetamide, a compound of formula (XII):

$$R_0 - \overset{CH_3}{\underset{CH_3}{\overset{|}{\underset{|}{N^\oplus}}}} - CH_2 - C_6H_5 \quad Cl^\ominus \quad (XII)$$

in which:

$R_0$ denotes a $C_{12}$–$C_{18}$ alkyl radical or a mixture of such alkyl radicals, such as the $C_{12}$–$C_{14}$ and $C_{14}$–$C_{16}$ mixtures.

The preserving agent in the compositions according to the invention is generally at a concentration of between 0.002 and 0.8% by weight and, preferably, between 0.02 and 0.5% by weight.

The pH of the compositions according to the invention is generally between 7 and 8.5 and, preferably, between 7 and 8; it is obtained with the aid of a buffer such as, for example, a phosphate buffer (dipotassium hydrogen phosphate/potassium dihydrogen phosphate).

The compositions according to the invention may also contain other traditional adjuvants such as, for example, moistening agents, softening agents, perfumes or colorants, these, of course, being characterized by being stable in the composition and not causing irritation or smarting of the ocular mucosa.

Among the moistening agents there may be mentioned, in particular, 2-methyl-2,4-pentanediol and polyethylene glycol with a molecular weight of approximately 600.

Among the softening agents there may be mentioned, in particular, allantoin and azulene.

To improve the understanding of the subject of the invention, several embodiments will now be described by way of examples which are purely illustrative and do not imply any limitation.

EXAMPLE 1

A lotion for removing eye make-up, formulated as follows, is prepared:

Amphoteric organic compound, sold under the trade names "Miranol C2M Conc. N.P.", "Miranol C2M Conc. O.P." or "Miranol CM Special" by the company "Miranol" and denoted by the formula:

| | | |
|---|---|---|
| 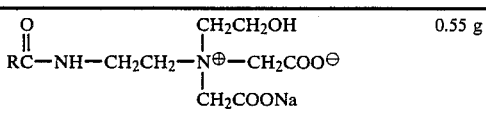 | | 0.55 g |
| in which RCO— denotes a residue of coprah fatty acids | | |
| Ammonium laurylsulphate, sold under the trade name "Texapon A-400" by the company | | 0.45 g |
| "Henkel" | | |
| Aqueous solution containing 15% by weight of polyacrylamidomethylpropanesulphonic acid, sold under the trade name "Cosmedia Polymer HSP-1180" by the company "Henkel" | | 6.0 g |
| Triethanolamine | | 0.5 g |
| Allantoin | | 0.05 g |
| 2-Methyl-2,4-pentanediol | | 1 g |
| Sodium ethylmercurythiosalicylate | | 0.003 g |
| Perfume | | 0.1 g |
| Sterile demineralized water q.s. | | 100 g |

This lotion has a pH of approximately 8.

This lotion, applied in the evening before bed time, enables make-up to be removed rapidly without irritating the region around the eyes.

EXAMPLE 2

A lotion for removing eye make-up, formulated as follows, is prepared:

Product sold under the trade name "Miranol MHT" by the company "Miranol" and containing the amphoteric organic compound of formula:

| | | |
|---|---|---|
| 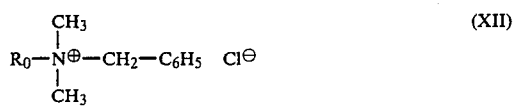 | | 1 g |
| and the sodium salt of tridecyl alcohol sulphated and oxyethylenated with 1–4 moles of ethylene oxide | | |
| Sodium salt of lauryl alcohol carboxylated and oxyethylenated with 13 moles of ethylene oxide, sold under the trade name "Sandopan LS 24" by the company "Sandoz" | | 0.4 g |
| Poly-  -alanine, prepared according to example 1 of Belgian patent No. 893,738 | | 0.8 g |
| Allantoin | | 0.05 g |
| 2-Methyl-2,4-pentanediol | | 1 g |
| Potassium dihydrogen phosphate | | 0.1 g |
| Dipotassium hydrogen phosphate | | 0.3 g |
| Methyl para-hydroxybenzoate | | 0.15 g |
| Perfume | | 0.1 g |
| Sterile demineralized water q.s. | | 100 g |

This lotion has a pH of 7.3.

This lotion is especially suitable for removing make-up from the eyes without tending to stick the eyelashes and the eyelids of the users.

EXAMPLE 3

A lotion for removing eye make-up, formulated as follows, is prepared:

Amphoteric organic compounds sold under the trade names "Miranol C2M Conc. N.P.", "Miranol C2M Conc. O.P." or "Miranol CM Special" by the company "Miranol", and denoted by the formula:

| | | |
|---|---|---|
| $\overset{O}{\underset{}{\overset{\|}{RC}}} - NH - CH_2CH_2 - \overset{CH_2CH_2OH}{\underset{CH_2COONa}{\overset{\|}{\underset{\|}{N^\oplus}}}} - CH_2COO^\ominus$ | | 0.7 g |
| In which RCO— denotes a residue of coprah fatty acids | | |
| Magnesium salt of laurylsulphate oxyethylenated with 1–4 moles of ethylene oxide, sold under the trade name "Texapon MG" by the company "Henkel" | | 0.55 g |
| Poly-1³-alanine prepared according to Example of Belgian patent No. 893,738 | | 0.7 g |
| Triethanolamine | | 0.08 g |
| Allantoin | | 0.05 g |

| | |
|---|---|
| 2-Methyl-2,4-pentanediol | 1 g |
| Sodium ethylmercurythiosalicylate | 0.003 g |
| Perfume | 0.1 g |
| Sterile demineralized water q.s. | 100 g |

This lotion has a pH of approximately 8.

It removes make-up well in a manner which is pleasant for the user.

EXAMPLE 4

A lotion for removing eye make-up, formulated as follows, is prepared:

Product sold under the trade name "Miranol 2 MHT Modified" by the company "Miranol" and containing the sodium salt of tridecylic acid which is sulphated and oxyethylenated with 1-4 moles of ethylene oxide, and the compound of formula:

| | |
|---|---|
| [structure] | 0.55 g |
| Monoethanolamine salt of sulphated lauryl alcohol, sold under the trade name "Texapon MLS" by the company "Henkel" | 0.45 g |
| Hydroxyethyl cellulose sold under the trade name "Natrosol 250" by the company "Hercules" | 0.2 g |
| Triethanolamine | 0.08 g |
| Allantoin | 0.05 g |
| 2-methyl-2,4-pentanediol | 1 g |
| Sodium ethylmercurythiosalicylate | 0.003 g |
| Perfume | 0.1 g |
| Sterile demineralized water q.s. | 100 g |

This lotion has a pH of approximately 8.

This lotion, used in the evening, removes make-up perfectly without causing any irritation to the eyelids.

EXAMPLE 5

A lotion for removing eye make-up, formulated as follows, is prepared:

Product sold under the trade name "Miranol MHT" by the company "Miranol" and containing the amphoteric organic compound of formula:

| | |
|---|---|
| [structure] | 0.4 g |
| and the sodium salt of tridecyl alcohol which is sulphated and oxyethylenated with 1-4 moles of ethylene oxide | |
| Ammonium laurylsulphate sold under the trade name "Texapon A-400" by the company "Henkel" | 0.3 g |
| Polyvinylpyrrolidone having a molecular weight of approximately 40,000 sold under the trade name "PVP K-30" by the company "GAF" | 0.5 g |
| Allantoin | 0.05 g |
| 2-Methyl-2,4-pentanediol | 1 g |
| Sodium ethylmercurythiosalicylate | 0.003 g |
| Perfume | 0.1 g |
| Sterile demineralized water q.s. | 100 g |

This lotion has a pH of 7.8.

This lotion permits rapid and very efficient removal of make-up without irritating the eyes.

We claim:

1. Cosmetic composition for removing eye make-up consisting essentially of an aqueous solution of a mixture of surface active agents said mixture comprising:

(1) from 0.05 to 3% by weight of at least one amphoteric surface-active agent selected from (a) the compounds of formula (I):

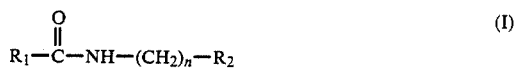

in which:

n is from 1 to 3;

$R_1$ denotes a fatty chain containing from 7 to 17 carbon atoms; and $R_2$ denotes a residue of formula (II) or (III):

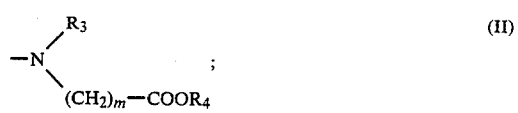

in which:

m is 1 or 2;

$R_5$ denotes a residue $-CH_2CH_2Or_4$ or a residue $-CH_2CH_2OCH_2CH_2COOR_4$;

$R_4$ denotes a hydrogen atom or an alkali metal;

$R_5$ denotes a $C_1-C_2$ alkyl or hydroxyalkyl residue; and $R_6$ denotes a $C_1-C_2$ alkyl or hydroxyalkyl residue or a residue $-(CH_2)_mCOOR_4$, (b) the compounds of formula (IV):

in which:

$R'_1$ denotes a fatty chain containing from 8 to 18 carbon atoms;

$R_7$ and $R_8$ denote, independently, a $C_1-C_2$ alkyl residue;

and (c) the compounds of formula (V), (VI) or (VII):

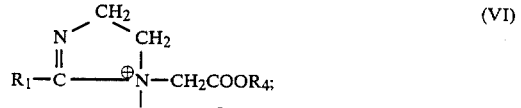

-continued

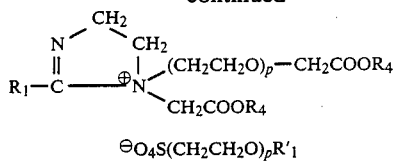

in which
R$_1$, R'$_1$ and R$_4$ are as defined in (a) and (b) above; and
p is from 0 to 4;

(2) from 0.05 to 3% by weight of at least one anionic surface-active agent selected from the compounds of formula (VIII), (IX), (X) and (XI):

$$R'_1-(OCH_2CH_2)_p-OSO_3R_9 \quad (VIII)$$

$$[R'_1-(OCH_2CH_2)_p-OSO_3]_2R_{10} \quad (IX)$$

$$R'_1-(OCH_2CH_2)_p-OSO_3H \cdot NR_{11}R_{12}R_{13} \quad (X)$$

$$R'_1-(OCH_2CH_2)_p-OCH_2COOR_9 \quad (XI)$$

in which:
R'$_1$ and p are as defined in (1) above;
R$_9$ denotes an alkali metal;
R$_{10}$ denotes an alkaline-earth metal;
R$_{11}$, R$_{12}$ and R$_{13}$ independently denote a hydrogen, a C$_1$-C$_3$ alkyl residue or a C$_1$-C$_3$ hydroxyalkyl residue;

(3) from 0.02 to 8% by weight of
(a) at least one nonionic polymer selected from polyalanines, (C$_1$-C$_3$-alkyl)cellulose, polyhydroxy-(C$_1$-C$_3$-alkyl)celluloses, polyvinylpyrrolidone, nonionic starch derivatives and hydroxypropylated derivatives of guar gum,
(b) at least one anionic polymer taken from the group consisting of polyacrylamides containing carboxylate groups, polyacrylamidosulphonic acid and its salts, and the polymers and homopolymers of acrylic or methacrylic acid and their salts, with a molecular weight of less than 100,000,
or
(c) a mixture of polymers (a) and (b) provided that the total concentration of the surface active agents in the composition does not exceed 5% by weight, the above percentages being calculated relative to the total weight of the composition.

2. A composition according to claim 1, consisting essentially of:
(1) from 0.1 to 2% by weight of at least one said amphoteric surface active agent;
(2) from 0.1 to 2% by weight of at least one said anionic surface active agent; and
(3) from 0.05 to 5% by weight of at least one said nonionic polymer, or at least one said anionic polymer or a mixture thereof.

3. A composition according to claim 1 wherein, in said amphoteric surface active agent formula (I), (V) or (VI) R$_1$ denotes a C$_{11}$-C$_{13}$ fatty chain, or in said amphoteric surface active agent of formula (IV) and in said anionic surface active agent of formulae (VIII) to (XI) R'$_1$ denotes a C$_{12}$-C$_{14}$ fatty chain.

4. A composition according to claim 1 wherein each said amphoteric surface active agent is selected from the compounds of the following formulae:

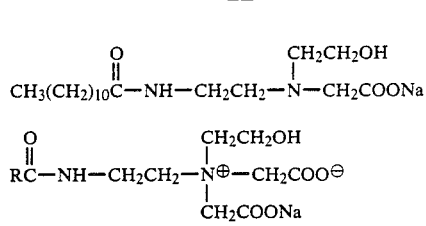

(a)

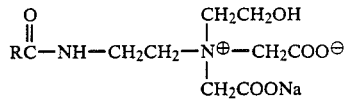

(b)

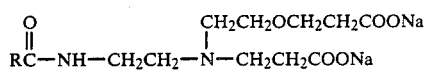

(c)

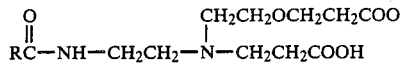

(d)

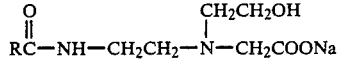

(e)

(f)

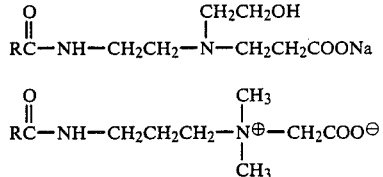

(g)

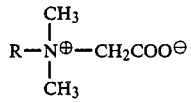

(h)

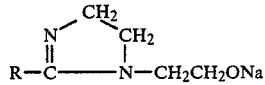

(i)

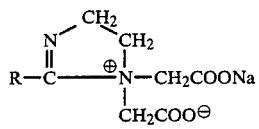

(j)

and

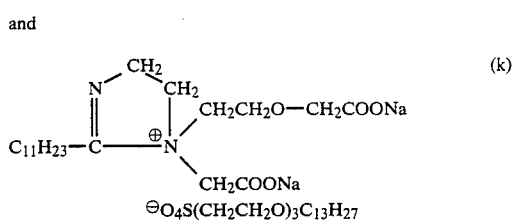

(k)

in which R, in the formulae (b) to (j), denotes a residue of coprah fatty acids.

5. A composition according to claim 1 wherein each said anionic surface active agent is selected from the compounds of the following formulae:

$$CH_3(CH_2)_{10}CH_2OSO_3NH_4 \quad (l)$$

$$[CH_3(CH_2)_{10}CH_2(OCH_2CH_2)_nOSO_3]_2Mg \quad (m)$$

$$CH_3(CH_2)_{10}CH_2OSO_3H \cdot H_2NCH_2CH_2OH \quad (n)$$

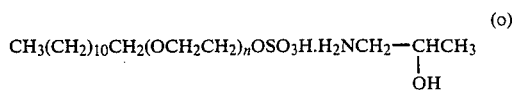

(o)

$$CH_3(CH_2)_{10}CH_2OSO_3Na \quad (p)$$

$CH_3(CH_2)_{12}CH_2(OCH_2CH_2)_nOSO_3Na$ (q)

$CH_3(CH_2)_{10}CH_2(OCH_2CH_2)_nOSO_3H.N(CH_2CH_2OH)_3$ (r)

$CH_3(CH_2)_{10}CH_2(OCH_2CH_2)_nOCH_2COONa$ (s)

and $C_{13}H_{27}(OCH_2CH_2)_nOSO_3Na$ (t)

in which n, in formulae (m) to (t), is from 1 to 4.

6. A composition according to claim 1 having a pH of from 7 to 8.5.

7. A composition according to claim 6 having a pH of from 7 to 8.

8. A composition according to claim 1 further including at least one preserving agent selected from sodium ethylmercurythiosalicylate, chlorohexidine salts, phenylmercury salts, a mixture consisting of 30% by weight of sodium benzoate and of 70% by weight of monochloroacetamide, and the compounds of formula (XII):

$$R_0 - \overset{CH_3}{\underset{CH_3}{\overset{|}{N^{\oplus}}}} - CH_2 - C_6H_5 \quad Cl^{\ominus}$$ (XII)

in which:

$R^0$ denotes a $C_{12}$–$C_{18}$ alkyl radical or a mixture of such alkyl radicals, such as the $C_{12}$–$C_{14}$ and $C_{14}$–$C_{16}$ mixtures.

9. A composition according to claim 8 wherein the concentration of preserving agent is from 0.002 to 0.8% by weight.

10. A composition according to claim 8 wherein the preserving agent is digluconate, diacetate or dihydrochloride salt of chlorohexidine.

11. A composition according to claim 8 wherein the preserving agent is phenylmercury nitrate.

12. A composition according to claim 4 wherein each said anionic surface active agent is selected from the compounds $CH_3(CH_2)_{10}CH_2OSO_3NH_4$ (l)

$[CH_3(CH_2)_{10}CH_2(OCH_2CH_2)_nOSO_3]_2Mg$ (m)

$CH_3(CH_2)_{10}CH_2OSO_3H.H_2NCH_2CH_2OH$ (n)

$CH_3(CH_2)_{10}CH_2(OCH_2CH_2)_nOSO_3H.H_2NCH_2-\underset{\underset{OH}{|}}{CHCH_3}$ (o)

$CH_3(CH_2)_{10}CH_2OSO_3Na$ (p)

$CH_3(CH_2)_{12}CH_2(OCH_2CH_2)_nOSO_3Na$ (q)

$CH_3(CH_2)_{10}CH_2(OCH_2CH_2)_nOSO_3H.N(CH_2H_2OH)_3$ (r)

$CH_3(CH_2)_{10}CH_2(OCH_2CH_2)_nOCH_2COONa$ (s)

and $C_{13}H_{27}(OCH_2CH_2)_nOSO_3Na$ (t)

in which:

n, in formulae (m) to (t), is from 1 to 4.

13. A composition according to claim 12 having a pH of from 7 to 8.5.

14. A composition according to claim 13 further including a preserving agent selected from sodium ethylmercurythiosalicylate, chlorohexidine salts, phenylmercury salts, a mixture consisting of 30% by weight of sodium benzoate and of 70% by weight of monochloroacetamide, and the compounds of formula (XII):

$$R_0 - \overset{CH_3}{\underset{CH_3}{\overset{|}{N^{\oplus}}}} - CH_2 - C_6H_5 \quad Cl^{\ominus}$$ (XII)

in which:

$R^0$ denotes a $C_{12}$–$C_{18}$ alkyl radical or a mixture of such alkyl radicals, such as the $C_{12}$–$C_{14}$ and $C_{14}$–$C_{16}$ mixtures.

15. A composition according to claim 14 containing from 0.002 to 0.8% by weight of said preserving agent.

16. A process for removing eye make-up comprising applying to said eye make-up, in an amount effective to remove said eye make-up, and eye make-up remover composition consisting essentially of (1) from 0.05 to 3% by weight of at least one amphoteric surface-active agent selected from (a) the compounds of formula (I):

$$R_1 - \overset{O}{\overset{\|}{C}} - NH - (CH_2)_n - R_2$$ (I)

in which:

n is from 1 to 3;

$R_1$ denotes a fatty chain containing from 7 to 17 carbon atoms; and $R_2$ denotes a residue of formula (II) or (III):

$$-N\overset{R_3}{\underset{(CH_2)_m - COOR_4}{\diagdown}}$$ (II)

$$-\overset{\oplus}{N}\overset{R_5}{\underset{R_6}{\diagdown}}-CH_2COO^{\ominus}$$ (III)

in which:

m is 1 or 2;

$R_5$ denotes a residue $-CH_2CH_2OR_4$ or a residue $-CH_2CH_2OCH_2COOR_4$; in which $R_1$, $R'_1$ and $R_4$ are as defined in (a) and (b) above; and p is from 0 to 4;

(2) from 0.05 to 3% by weight of at least one anionic surface-active agent selected from the compounds of formula (VIII), (IX), (X) or (XI):

$R'_1-(OCH_2CH_2)_p-OSO_3R_9$ (VIII)

$[R'_1-(OCH_2CH_2)_p-OSO_3]_2R_{10}$ (IX)

$R'_1-(OCH_2CH_2)_p-OSO_3H.NR_{11}R_{12}R_{13}$ (X)

$R'_1-(OCH_2CH_2)_p-OCH_2COOR_9$ (XI)

in which:

$R'_1$ and p are as defined in (1) above;

$R_9$ denotes an alkali metal;

$R_{10}$ denotes an alkaline-earth metal;

$R_{11}$, $R_{12}$ and $R_{13}$ independently denote hydrogen, a $C_1$-$C_3$ alkyl residue or a $C_1$-$C_3$ hydroxyalkyl residue;

(3) from 0.02 to 8% by weight of
- (a) at least one nonionic polymer selected from polyalanines, ($C_1$-$C_3$-alkyl) celluloses, polyhydroxy-($C_1$-$C_3$-alkyl) celluloses, polyvinylpyrrolidone, nonionic starch derivatives and hydroxypropylated derivatives of guar gum,
- (b) at least one anionic polymer taken from the group consisting of polyacrylamides containing carboxylate groups, polyacrylamidosulphonic acid and its salts, and the polymers and homopolymers of acrylic or methacrylic acid and their salts, with a molecular weight of less than 100,000, or
- (c) a mixture of polymers (a) and (b) provided that the total concentration of the surface active agents in the composition does not exceed 5% by weight, the above percentages being calculated relative to the total weight of the composition.

* * * * *